(12) United States Patent
Tsukagoshi et al.

(10) Patent No.: US 7,471,757 B2
(45) Date of Patent: Dec. 30, 2008

(54) X-RAY COMPUTED TOMOGRAPHIC APPARATUS, SCAN PLAN SUPPORT APPARATUS, AND PROGRAM

(75) Inventors: Shinsuke Tsukagoshi, Nasushiobara (JP); Yasuhiko Satomura, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 11/843,950

(22) Filed: Aug. 23, 2007

(65) Prior Publication Data

US 2008/0049889 A1 Feb. 28, 2008

(30) Foreign Application Priority Data

Aug. 25, 2006 (JP) ............................. 2006-229211

(51) Int. Cl.
*A61B 6/00* (2006.01)
(52) U.S. Cl. .......................................... 378/4; 378/901
(58) Field of Classification Search ............... 378/4–20, 378/901
See application file for complete search history.

(56) References Cited

U.S. PATENT DOCUMENTS

| | | | |
|---|---|---|---|
| 7,031,423 B2 | 4/2006 | Tsukagoshi | |
| 2002/0007117 A1 | 1/2002 | Ebadollahi et al. | |
| 2002/0080918 A1 | 6/2002 | Sako | |
| 2003/0123603 A1 | 7/2003 | Suzuki | |
| 2003/0161435 A1 | 8/2003 | Ozaki | |
| 2004/0013223 A1* | 1/2004 | Yamazaki et al. | 378/4 |
| 2004/0171924 A1 | 9/2004 | Mire et al. | |
| 2004/0179644 A1* | 9/2004 | Tsuyuki | 378/8 |
| 2004/0202277 A1 | 10/2004 | Okumura et al. | |
| 2006/0104412 A1 | 5/2006 | Kawanabe | |

FOREIGN PATENT DOCUMENTS

JP  2004-329661  11/2004

* cited by examiner

*Primary Examiner*—Courtney Thomas
(74) *Attorney, Agent, or Firm*—Oblon, Spivak, McClelland, Maier & Neustadt, P.C.

(57) ABSTRACT

An X-ray computed tomographic apparatus includes an X-ray tube which generates X-rays, an X-ray detector which detects X-rays transmitted through a subject to be examined, a reconstruction device which reconstructs an image on the basis of an output from the X-ray detector, a scan plan execution processing unit which generates the data of a scan planning window including a timing chart which expresses a scan sequence including a plurality of scan elements corresponding to a plurality of scan conditions as a temporal change in tube current or dose index, and a display device which displays a scan planning window on the basis of the data.

17 Claims, 6 Drawing Sheets

X-RAY COMPUTED TOMOGRAPHIC APPARATUS, SCAN PLAN SUPPORT APPARATUS, AND PROGRAM

CROSS-REFERENCE TO RELATED APPLICATIONS

This application is based upon and claims the benefit of priority from prior Japanese Patent Application No. 2006-229211, filed Aug. 25, 2006, the entire contents of which are incorporated herein by reference.

BACKGROUND OF THE INVENTION

1. Field of the Invention

The present invention relates to an X-ray computed tomographic apparatus having a scan plan support function, a scan plan support apparatus, and a program.

2. Description of the Related Art

A scan planning window in a conventional X-ray computed tomographic apparatus displays the respective elements constituting a scan plan in a table form mainly comprising a text. A conventional X-ray computed tomographic apparatus can only perform imaging in the Z direction (body axis direction) within a small range of several tens of millis (40 mm etc.) at a time, and hardly performs time-series imaging, i.e., a so-called dynamic scan.

Recent X-ray computed tomographic apparatuses, however, generally perform a scan under various conditions at once owing to an increase in the number of rows of detectors and a reduction in imaging time. For example, multi-slice CT using 256 or more rows of flat panel detectors which are wide in the slice direction, in particular, has greatly increased the number of scan mode options and considerably increased the imaging speed. It is therefore useful to plan more scans such as dynamic imaging, S & S scan, and helical scan altogether as a sequence.

For this reason, a "scan plan displayed in a table form" provides good operability and visibility with respect to scan conditions for each scan, e.g., a scan time and a tube current, but presents difficulty in intuitively and clearly understanding the overall scan sequence, e.g., the order of scans and scan intervals.

BRIEF SUMMARY OF THE INVENTION

It is an object of the present invention to improve the visibility and operability of a scan plan in an X-ray computed tomographic apparatus.

An X-ray computed tomographic apparatus according to an aspect of the present invention comprises an X-ray tube which generates X-rays, an X-ray detector which detects X-rays transmitted through a subject to be examined, a reconstruction processing unit which reconstructs an image on the basis of an output from the X-ray detector, a scan planning unit which generates data of a scan planning window including a timing chart expressing as a temporal change in tube current or dose index a scan sequence including a plurality of scan elements corresponding to a plurality of scan conditions, and a display unit which displays the scan planning window on the basis of the data.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

An embodiment of the present invention will be described with reference to the views of the accompanying drawing. In order to reconstruct one-slice tomographic image data, projection data corresponding to one rotation around a subject to be examined, i.e., about 360°, is required, or (180°+view angle) projection data is required in the half scan method. The present invention can be applied to either of these reconstruction schemes. The half scan scheme will be exemplified here. As mechanisms of converting incident X-rays into electric charges, the following techniques are the mainstream: an indirect conversion type that converts X-rays into light through a phosphor such as a scintillator and converts the light into electric charges through photoelectric conversion elements such as photodiodes, and a direct conversion type that uses generation of electron-hole pairs in a semiconductor by X-rays and migration of the electron-hole pairs to an electrode, i.e., a photoconductive phenomenon. As an X-ray detection element, either of these schemes can be used. In this case, the former type, i.e., the indirect conversion type, will be exemplified. Recently, with an increase in the number of rows of detectors, detectors including 64 rows (40 mm) or more have been put into practice. The present invention can be applied to an X-ray computed tomographic apparatus comprising a multi-slice type detector as well as a conventional X-ray computed tomographic apparatus comprising a single-slice type detector. The X-ray computed tomographic apparatus comprising the single-tube type detector will be exemplified here.

Figure 1:
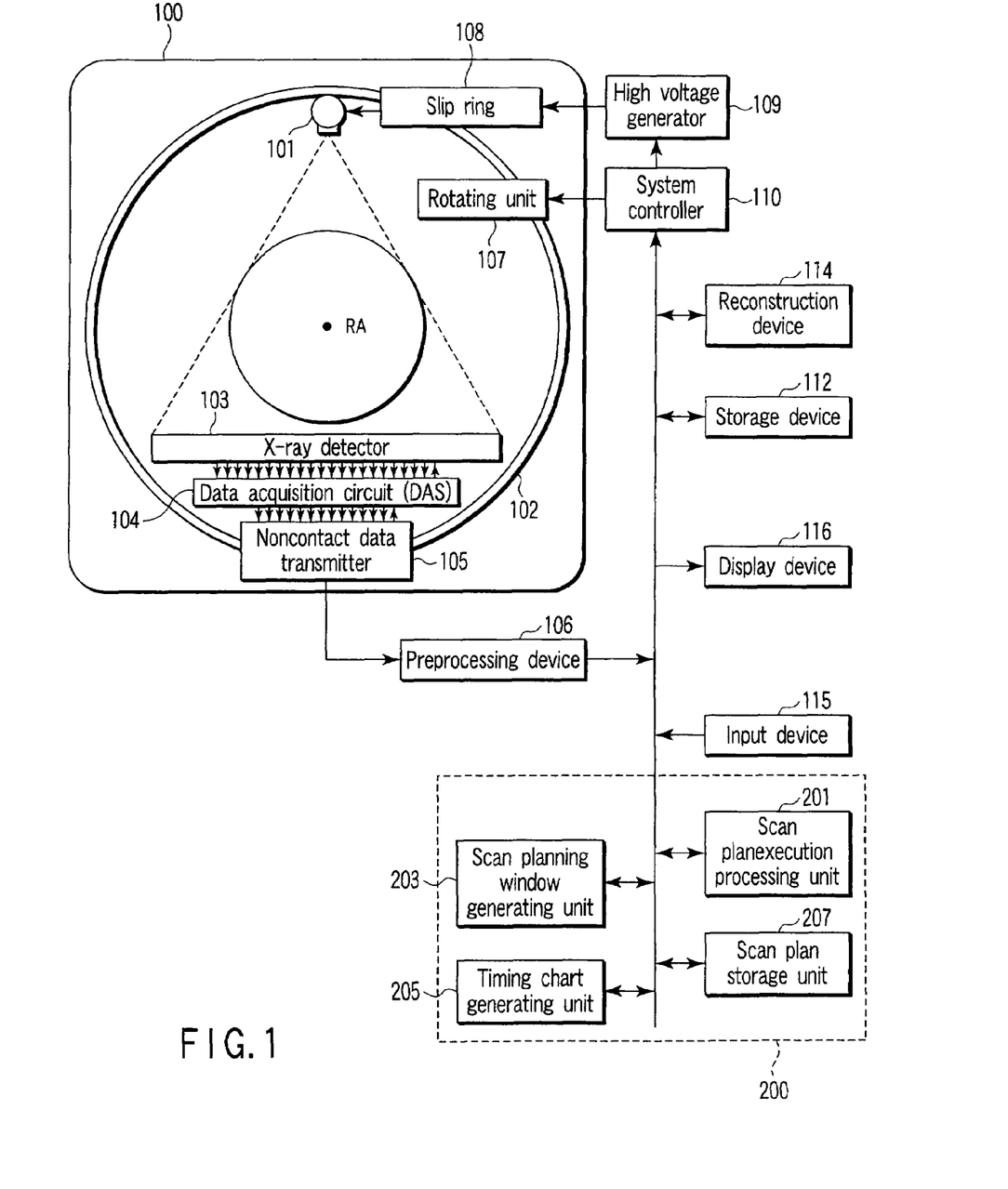
FIG. 1 is a block diagram showing the arrangement of an X-ray computed tomographic apparatus according to an embodiment of the present invention.

FIG. 1 shows the arrangement of an X-ray computed tomographic apparatus according to this embodiment. A gantry 100 has an X-ray tube 101 and X-ray detector 103 of a so-called multi-row type (also called a two-dimensional array type detector or flat panel detector) comprising, for example, 64 or 256 rows. The X-ray tube 101 and X-ray detector 103 are mounted on an annular frame 102 which is rotatably supported around a rotation axis RA. The X-ray detector 103 faces the X-ray tube 101. A rotating unit 107 rotates the frame 102 at a high speed of, for example, 0.4 sec/rotation. A high voltage generator 109 applies a tube voltage to the X-ray tube 101 through a slip ring 108 and supplies a filament current to the X-ray tube 101. With this operation, the X-ray tube 101 generates X-rays. The X-ray detector 103 detects X-rays transmitted through the subject.

A data acquisition circuit 104 generally called a DAS (Data Acquisition System) converts a signal output from the X-ray detector 103 for each channel into a voltage signal, amplifies it, and further converts it into a digital signal. This data (raw data) is sent to a preprocessing device 106 housed in a console outside the gantry 100 through a noncontact data transmitter 105. The preprocessing device 106 performs correction processing such as sensitivity correction for the raw data. A storage device 112 then stores the resultant data as so-called projection data at a stage immediately before reconstruction processing.

The storage device 112 is connected to a system controller 110 through a data/control bus, together with a reconstruction device 114, display device 116, input device 115, and scan plan support apparatus 200. The scan plan support apparatus 200 includes a function for supporting an imaging technician to develop a scan plan. For this purpose, the scan plan support apparatus 200 comprises a scan plan execution processing unit 201 which is in charge of overall operation control on scan planning and various types of computation processing, a scan plan storage unit 207 for storing the data of a plurality of scan plans, the data of a developed plan, and the like, a scan planning window generating unit 203 for generating the data of a scan planning window to be described later, and a timing chart generating unit 205 which generates a timing chart for a scan sequence (to be described later).

Note that in this case, a unit of scan operation controlled under unitary scan conditions will be referred to as a scan element. One examination comprises a plurality of scan elements. A plurality of scan elements constituting one examination are ranked. A train of a plurality of scan elements will be referred to as a scan sequence. A plurality of sets of scan conditions correspond to a plurality of scan elements. However, a plurality of sets of scan conditions do not always differ from each other, and may include the same scan conditions.

Scan conditions include many setting items such as a scan mode which discriminates the type of scan, a tube voltage, a tube current, the diameter (S-FOV) of an imaging field, the diameter (D-FOV) of a reconstruction field, an imaging slice thickness, a reconstruction slice thickness, a helical pitch, the number of slices, a start time representing an elapsed time from the start time point of a scan, a wait time representing the time interval between adjacent scan elements, and a pause time representing the intervals of X-ray generation within a scan element in S & S or the like. The scan modes typically include scanography, a dynamic scan, a 4D dynamic scan, an S & S scan, and a helical scan. A 4D dynamic scan is the operation of continuously scanning the same portion by using the flat panel detector 103.

Optimization of such scan conditions is a difficult task requiring a broad and highly sophisticated range of technical knowledge. A specialized system developed to support such setting is a so-called scan expert system. One of the main functions of this system is to receive an examination object and an examination region in addition to the sex, age, and physique of a subject to be examined and provide one or two or more scan sequence plans corresponding to the received information. The scan plan support apparatus 200 of this embodiment corresponds to this scan expert system. One of the important characteristic functions of the scan plan support apparatus 200 is to form a new window for scan plan setting operation.

Figure 2:
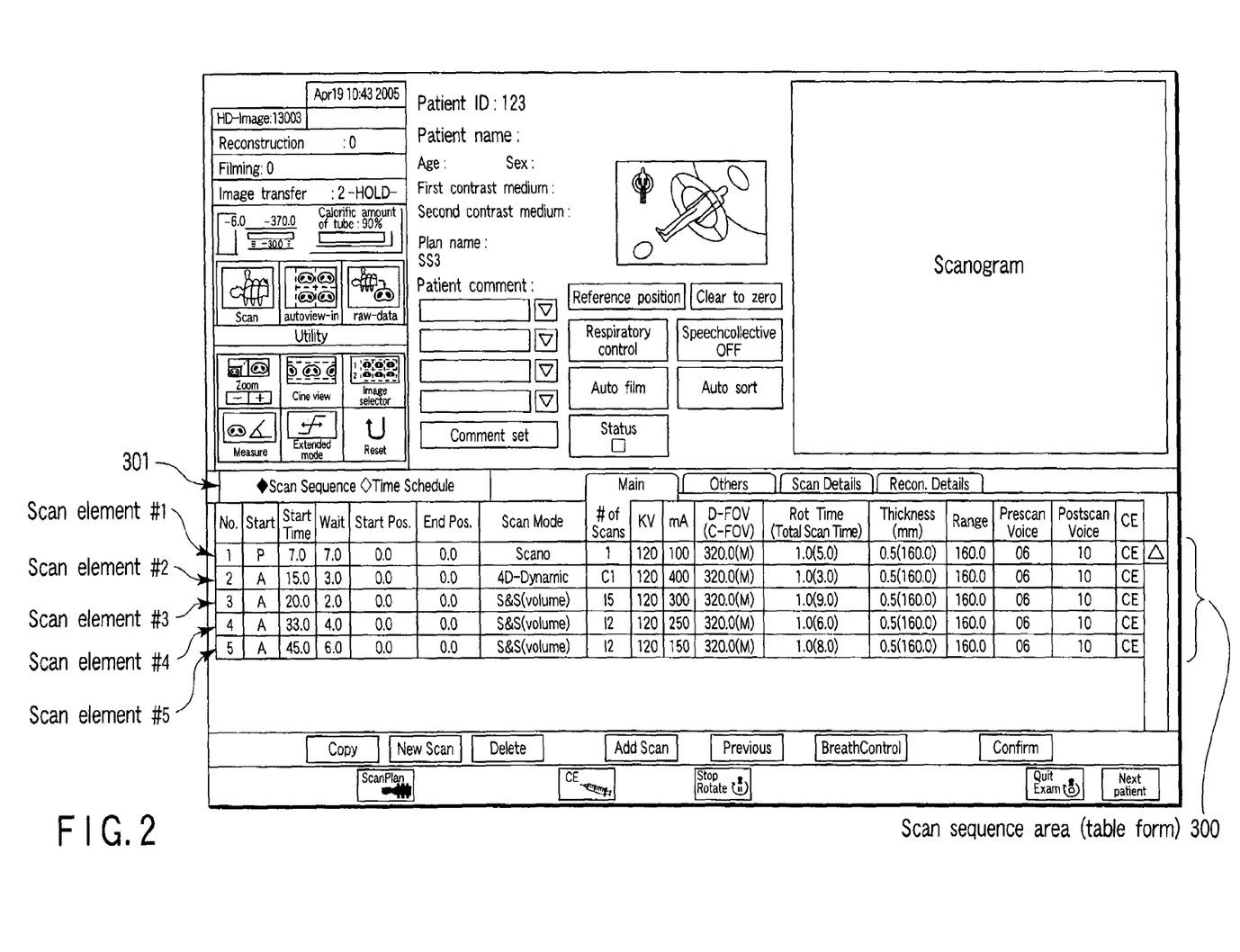
FIG. 2 is a view showing an example of a scan planning window including a scan sequence in table form which is generated by a scan plan execution processing unit FIG. 1.

As shown in FIG. 2, a plurality of scan elements #1 to #5 are arranged in a table form in the scan planning window generated by the scan planning window generating unit 203 of the scan plan support apparatus 200. The main categories of this table include many items such as:

scan element number start type (Start: manual (P)/automatic (A))

start time (Start Time) corresponding to elapsed time of each scan element after trigger operation for scan start wait time (Wait) as interval from end of immediately preceding scan element to start of scan element scan start position (Start Pos.) of each scan element scan end position (End Pos.) of each scan element scan mode (Scan Mode) which discriminates scan type number of scans in scan element (# of scans written as 1 or C1 in the scanographic mode, dynamic mode, and helical mode, which represents that X-ray are continuously generated during a scan element period, and as I5 or the like in the S & S mode, which represents that five X-ray pulses are generated at predetermined intervals (pause times))

tube voltage (kV)

tube current (mA)

diameter (D-FOV) of reconstruction field scan time (to be also referred to as a rotation time (Rotation Time)) required for X-ray tube to rotate once total scan time (Total Scan Time: simply given as a time width during which X-rays are generated in the scanographic mode, dynamic mode, and helical mode, and given as the total time obtained by adding the time obtained by multiplying a pause time by the number of pauses to the time obtained by multiplying a rotation time by the number of scans)

imaging slice thickness (Thickness)

These items are written as numerical values or symbols. As described above, in the current tendency toward a larger number of scan elements constituting a scan sequence, if scan elements are written in a table form as shown in FIG. 2, it is difficult to intuitively understand the temporal flow of an overall scan sequence.

Figure 3:
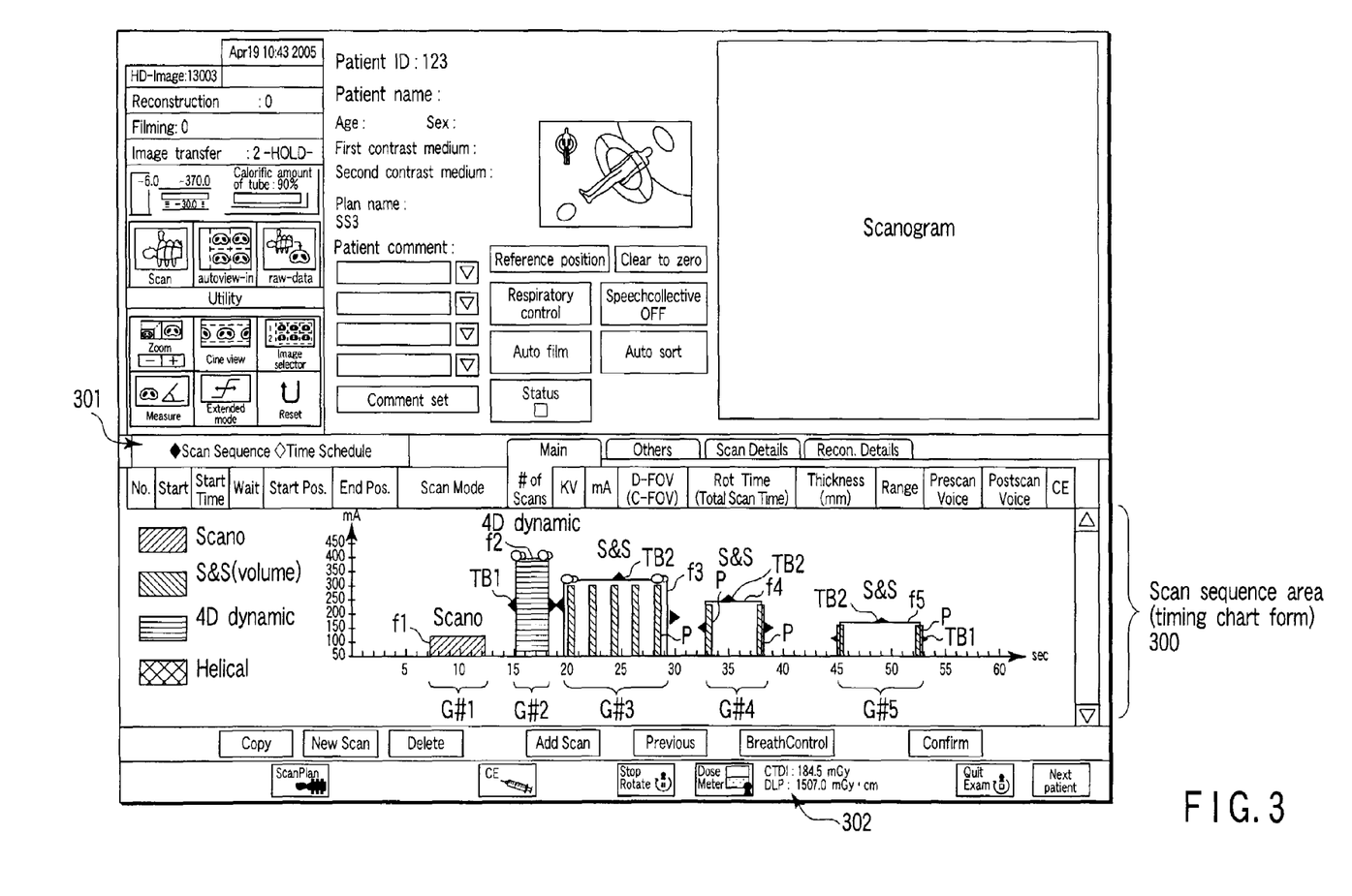
FIG. 3 is a view showing an example of a scan planning window including a scan sequence in a timing chart which is generated by the scan plan execution processing unit FIG. 1.

In this embodiment, therefore, as shown in FIG. 3, the timing chart generating unit 205 of the scan plan support apparatus 200 generates a timing chart which expresses a san sequence formed by ranking a plurality of scan elements subjected to scan control under a plurality of scan conditions as a temporal change in tube current or dose index (CTDI etc.), and generates the data of a scan planning window including the timing chart.

As shown in FIGS. 2 and 3, a scan planning window includes a scan sequence area 300 together with basic information such as patient information, utility information, the calorific amount limit of the X-ray tube, and a scanogram. In the scan sequence area 300, a plurality of scan elements #1 to #5 constituting a scan sequence are selectively arranged in table form or timing chart form in accordance with the operation of a display form switching button 301.

The abscissa and ordinate of the timing chart respectively represent the time and tube current (mA). A tube current (mA) can be replaced by another index representing a dose. Such another index is, for example, mAs (an index indicating a total tube current value corresponding to a scan time, which is calculated from a tube current set in an examination plan and an actual emission time), CTDIw (Computed Tomography Dose Index Weighted: an emission dose per unit slice thickness), or DLP (Dose Length Product: a total emission dose).

Scan elements #1 to #5 are respectively expressed by graphic patterns G#1 to G#5. The respective scan modes are written in a character form with the graphic patterns G#1 to G#5. The graphic patterns G#1 to G#5 respectively have frames f1 to f5 respectively having widths from the start times of the respective modes to the times when total scan times elapse and heights corresponding to the respective tube current values. The entire internal areas of the frames f1 and f2 corresponding to the scanographic mode and the dynamic mode or the helical mode are painted out in display forms corresponding to the respective scan modes. For example, display colors and hatchings are selectively used in accordance with scan modes. In the S & S mode, the frames f3, f4, and f5 each internally have posts P corresponding to the number of scans. Each post P has a width corresponding to a scan time and is painted out in a display form corresponding to the scan mode. The posts P are arranged at intervals corresponding to pause times.

Pointing and moving the frames f1 to f5 of the graphic patterns G#1 to G#5 with a pointing device such as a mouse can, for example, change the scan start times or the order of the scan element train. Tool buttons TB1 for prolonging or shortening a scan time are written on the left and right sides of each of the frames f1 to f5 of the graphic patterns G#1 to G#5. The operator can prolong or shorten the scan time of a given scan element by dragging the tool button TB1 to the left or right while pointing the pointer at the tool button TB1 with a pointing device such as a mouse. Tool buttons TB2 for adjusting the magnitude of a tube current are written on the upper portions of the frames f1 to f5 of the graphic patterns G#1 to G#5. The operator can adjust the magnitude of a tube current in a given scan element by dragging the tool button TB2 in the vertical direction while pointing the pointer at the tool button with a pointing device such as a mouse. The dose index (CTDI, DLP) is re-calculated and displayed in real time according to the adjustment of a tube current. In the S & S mode, the operator can adjust the length of a pause time by dragging the post P in the frame f3, f4, or f5 to the left and right while pointing the pointer at the post P with a pointing device such as a mouse.

Figure 4:
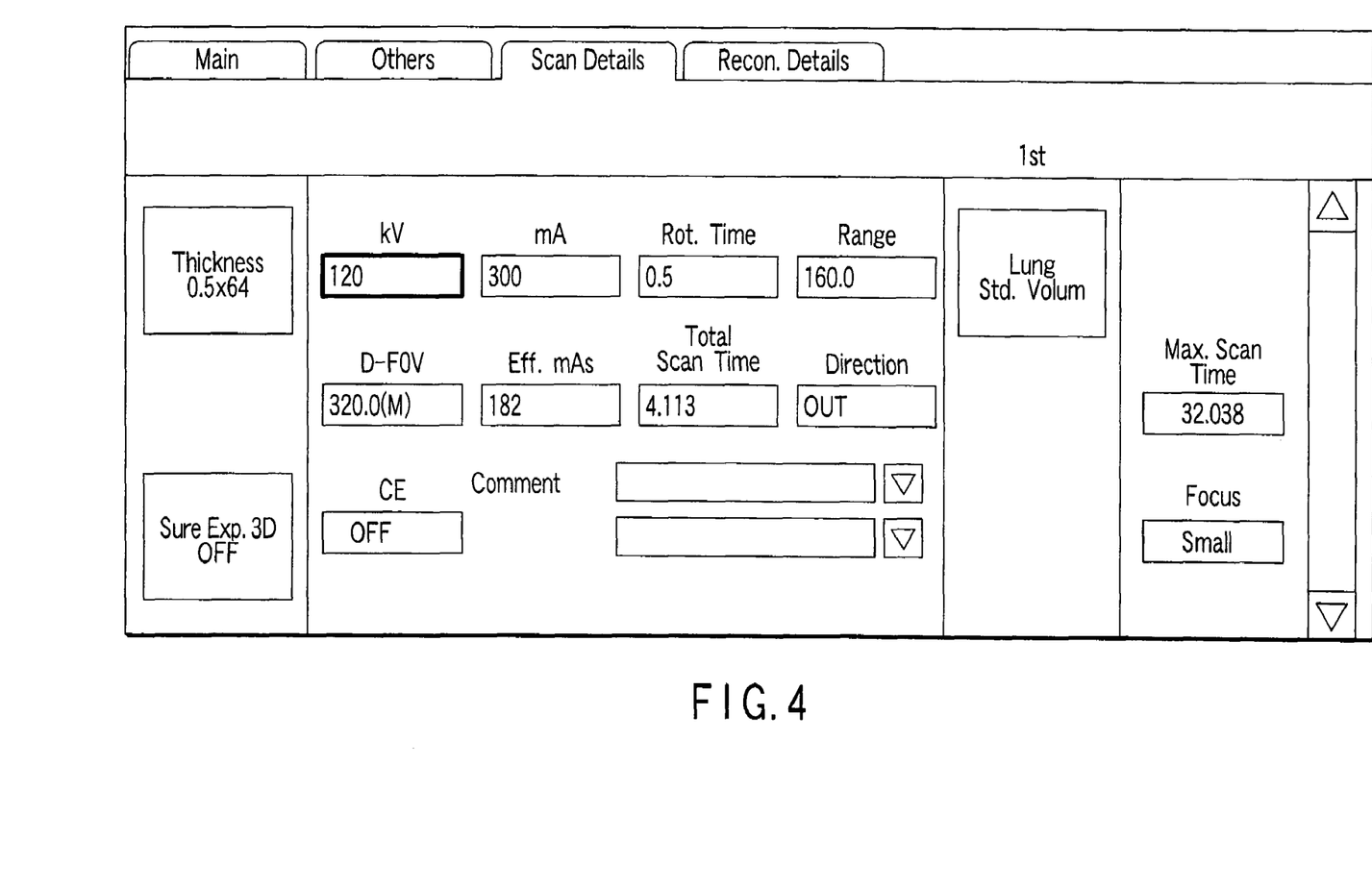
FIG. 4 is a view showing a scan condition details setting window which pops up when an operator performs predetermined operation on the timing chart in FIG. 3.

Performing specific operation, e.g., operating the right button of the mouse at an arbitrary position in one of the frames f1 to f5 of the graphic patterns G#1 to G#5 will pop up a details setting window like that shown in FIG. 4. This details setting window includes input boxes for items such as a tube voltage (kV), a tube current (mA), a scan time (rotation time), the diameter (D-FOV) of a reconstruction field, effective mAs, and a total scan time. The operator can input numerical values as the respective items.

Figure 5:
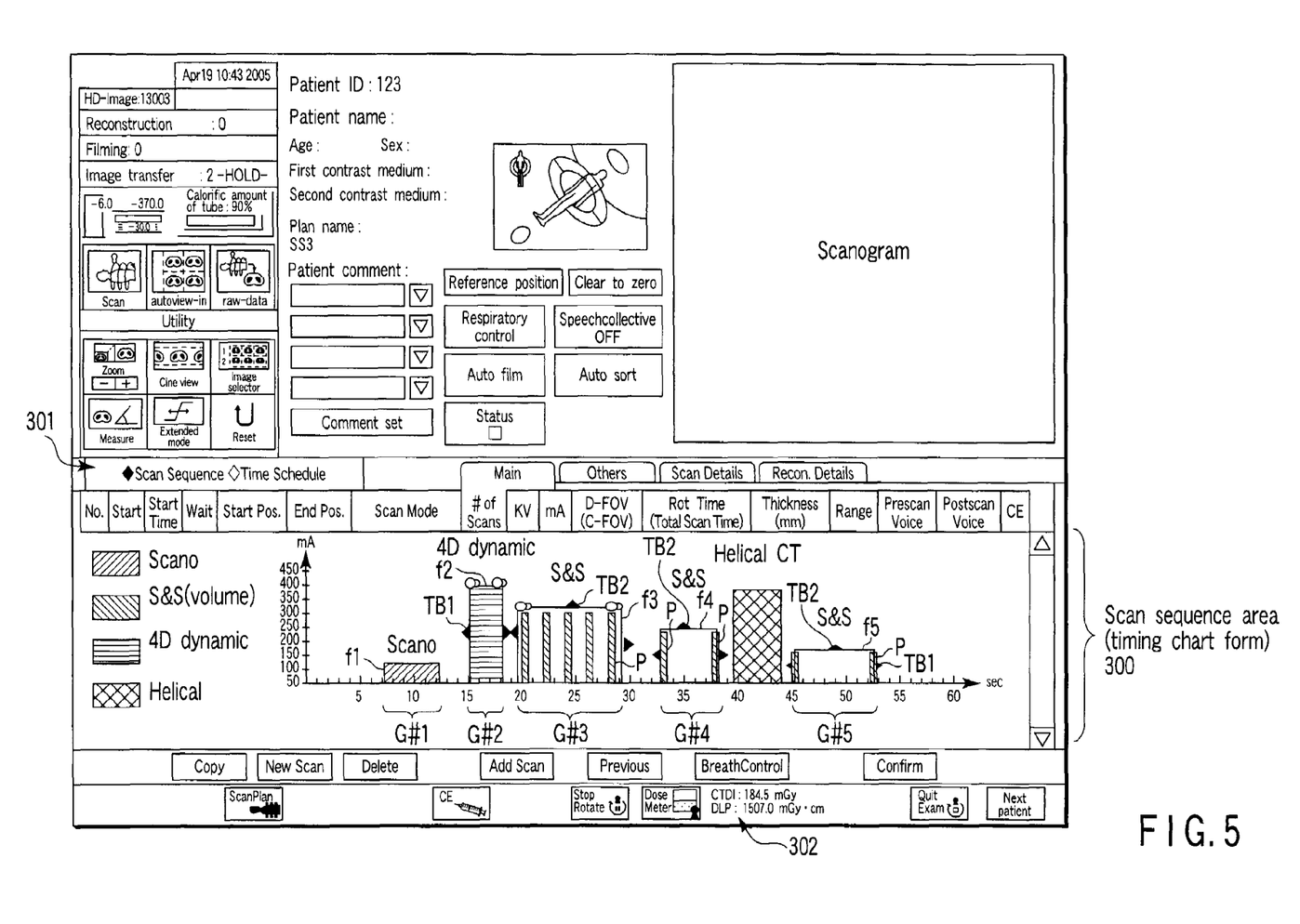
FIG. 5 is a view showing a timing chart obtained by scan element adding operation in this embodiment.

As shown in FIG. 5, the lower part of the scan sequence area of the window has command buttons for copying (copy), adding (New Scan), and deleting (Delete) for each scan element. For example, operating such a command button makes it possible to add a scan element in the helical scan mode, as shown in FIG. 5.

As described above, in this embodiment, visually expressing a single examination (scan sequence) as a timing chart as a whole by using graphic patterns allows the operator to intuitively and easily understand the scan sequence, thereby improving the visibility of a scan plan. Operating graphic patterns on the timing chart makes it possible to change each scan condition for a scan element, change the order of scan elements or the like, and copy, add, or delete a scan element. It is therefore possible to expect an improvement in operability.

Figure 6:
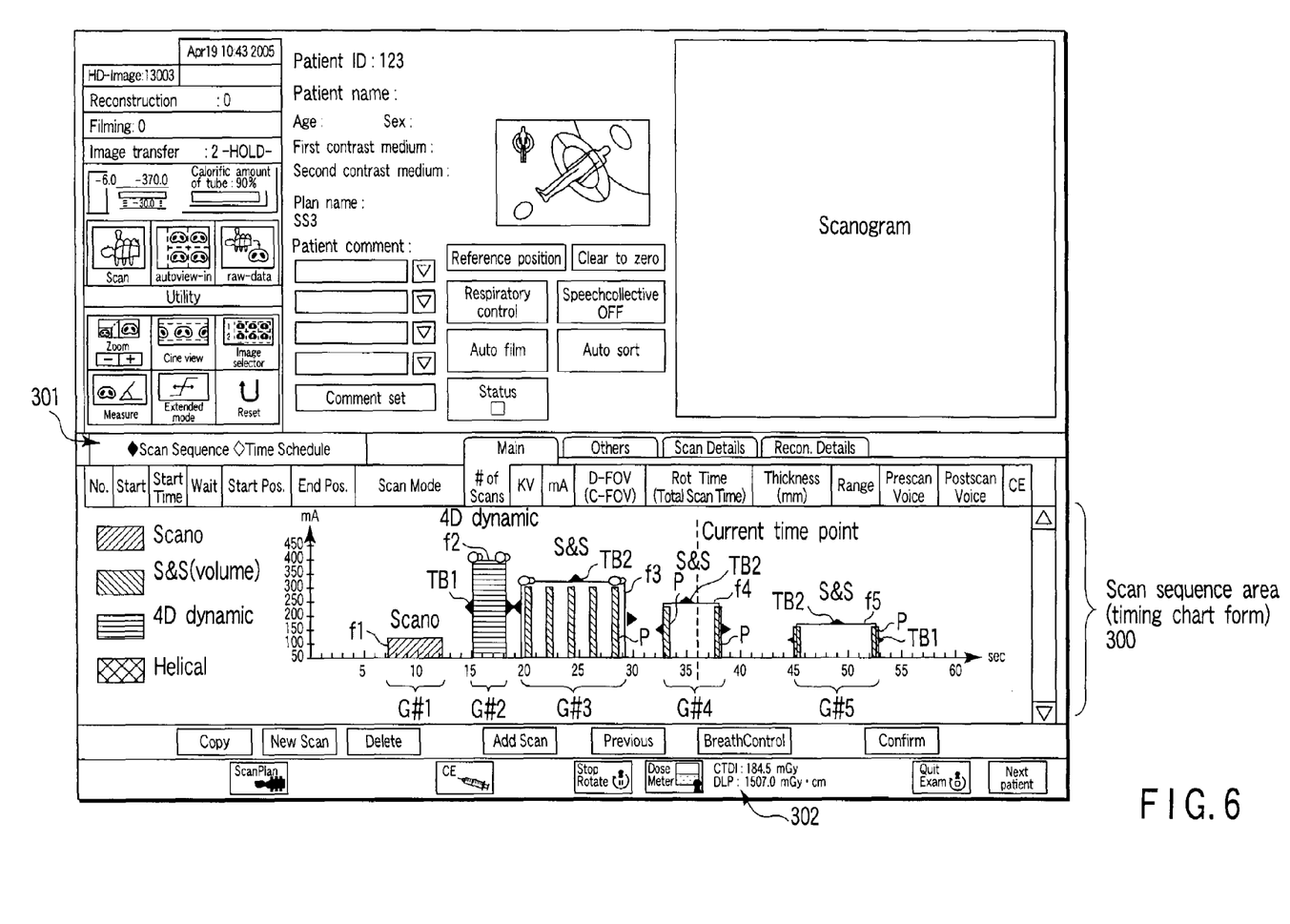
FIG. 6 is a view showing a line marker which is superimposed on a timing chart and moves with the lapse of time after scan start.

Note that even after the operator presses the scan trigger to actually start a scan, this apparatus displays a timing chart, and the scan planning window generating unit 203 superimposes a line marker corresponding to the current time point on the timing chart in accordance with a scan control signal from the system controller 110, as shown in FIG. 6. Since this line marker moves on the timing chart with the lapse of time, the imaging technician can intuitively understand the progress of a scan, scan conditions for the next scan, and the like at a glance.

Note that the present invention is not limited to the above embodiment, and constituent elements can be variously modified and embodied at the execution stage within the spirit and scope of the invention. Various inventions can be formed by proper combinations of a plurality of constituent elements disclosed in the above embodiments. For example, several constituent elements may be omitted from the all the constituent elements in each embodiment. In addition, constituent elements of the different embodiments may be combined as needed.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An X-ray computed tomographic apparatus comprising:
an X-ray tube which generates X-rays;
an X-ray detector which detects X-rays transmitted through a subject to be examined;
a reconstruction processing unit which reconstructs an image on the basis of an output from the X-ray detector;
a scan planning unit which generates data of a scan planning window including a timing chart, the timing chart expressing a scan sequence as a temporal change in tube current or another dose index, and the scan sequence including a plurality of scan elements corresponding to a plurality of scan conditions; and
a display unit which displays the scan planning window on the basis of the data.

2. An apparatus according to claim 1, wherein the scan planning unit changes a display form of the scan element on the timing chart in accordance with a scan mode.

3. An apparatus according to claim 1, wherein the scan planning unit changes a display color of the scan element on the timing chart in accordance with a scan mode.

4. An apparatus according to claim 1, wherein the scan planning window includes a command button for switching a display form of the scan sequence from the timing chart to a table form.

5. An apparatus according to claim 4, wherein the scan planning window includes a command button for switching a display form of the scan sequence from the table form to the timing chart.

6. An apparatus according to claim 1, wherein a command marker for commanding correction of a scan condition for each scan element is written beside the timing chart.

7. An apparatus according to claim 1, wherein a marker for increasing/decreasing a tube current for said each scan element is written beside the timing chart.

8. An apparatus according to claim 1, wherein a marker for increasing/decreasing a scan time for said each scan element is written beside the timing chart.

9. An apparatus according to claim 1, wherein a line marker which moves with a lapse of time after scan start is superimposed on the timing chart.

10. An apparatus according to claim 1, wherein the scan sequence includes a scan element corresponding to a 4D dynamic scan of continuously scanning the same portion with a flat panel detector.

11. An apparatus according to claim 1, wherein the scan planning window includes a total exposure dose indication associated with said plurality of scan elements.

12. An apparatus according to claim 7, wherein the scan planning window includes a total exposure dose indication associated with said plurality of scan elements, the total exposure dose indication is re-calculated and displayed in real time according to the increasing/decreasing of the tube current.

13. An X-ray computed tomographic apparatus comprising:
   an X-ray tube which generates X-rays;
   an X-ray detector which detects X-rays transmitted through a subject to be examined;
   a reconstruction processing unit which reconstructs an image on the basis of an output from the X-ray detector;
   a data generating unit which generates data of a temporal change in tube current associated with a plurality of scan elements corresponding to a plurality of scan conditions; and
   a display unit which displays a temporal change in the tube current.

14. A scan plan support apparatus which supports to develop a scan plan for X-ray computed tomography, comprising:
   a scan planning unit which generates data of a scan planning window including a timing chart, the timing chart expressing a scan sequence as a temporal change in tube current or another dose index, and the scan sequence including a plurality of scan elements corresponding to a plurality of scan conditions; and
   a display unit which displays the scan planning window on the basis of the data.

15. A scan plan support apparatus which supports to develop a scan plan for X-ray computed tomography, comprising:
   a data generating unit which generates data of a temporal change in tube current associated with a plurality of scan elements corresponding to a plurality of scan conditions; and
   a display unit which displays a temporal change in the tube current.

16. A computer readable medium including a computer executable program, which, when executed by a processor, causes the processor to perform steps comprising:
   developing a scan plan for X-ray computed tomography,
   inputting data of a scan sequence comprising a plurality of scan elements corresponding to a plurality of scan conditions,
   generating data of a scan planning window including a timing chart expressing the scan sequence as a temporal change in tube current or dose index on the basis of the data, and
   displaying the scan planning window.

17. A computer readable medium including a computer executable program, which, when executed by a processor, causes the processor to perform steps comprising: developing a scan plan for X-ray computed tomography,
   inputting data of a plurality of scan elements corresponding to a plurality of scan conditions,
   generating data of a temporal change in tube current on the basis of the data, and
   displaying the temporal change in the tube current.

* * * * *